United States Patent [19]
Cookson et al.

[11] Patent Number: 6,114,151
[45] Date of Patent: Sep. 5, 2000

[54] DETECTION OF A VARIANT FORM OF HIGH AFFINITY RECEPTOR TO IGE FCεRIβ USING PRIMERS AND PROBES

[75] Inventors: William O. C. Cookson; Michael R. Hill, both of Oxford, United Kingdom

[73] Assignee: ISIS Innovation Limited, Oxford, United Kingdom

[21] Appl. No.: 09/029,196

[22] PCT Filed: Aug. 29, 1996

[86] PCT No.: PCT/GB96/02095

§ 371 Date: Feb. 25, 1998

§ 102(e) Date: Feb. 25, 1998

[87] PCT Pub. No.: WO97/08338

PCT Pub. Date: Mar. 6, 1997

[30] Foreign Application Priority Data

Aug. 29, 1995 [GB] United Kingdom ............... 9517585

[51] Int. Cl.⁷ ............... C12P 19/34; C12Q 1/68; C07H 21/04
[52] U.S. Cl. ............ 435/91.2; 435/6; 435/91.1; 536/23.1; 536/23.5; 536/24.3; 536/24.31; 536/24.33
[58] Field of Search ............... 435/6, 91.1, 91.2; 536/23.1, 23.5, 24.3, 24.31, 24.33

[56] References Cited

FOREIGN PATENT DOCUMENTS

| 0 649 910 | 4/1995 | European Pat. Off. . |
|---|---|---|
| 95 05481 | 2/1995 | WIPO . |

OTHER PUBLICATIONS

Kuster et al JBC vol. 267, No. 18, pp. 12782–12787, 1992.
Shirakawa et al Nature Genetics vol. 7 pp. 125–130, 1994.
Hill and Cookson, "A new variant of the β subunit of the high–affinity receptor for Immunoglobulin E (FcεRI–β E237G): associations with measures of atopy and bronchial hyper–responsiveness", Human Molecular Genetics 5(7):959–962 (1996).

Shirakawa et al, "Association between atopic asthma and a coding variant of FcεRI–β in a Japanese population ", Human Molecular Genetics 5(8):1129–1130 (1996).
Küster et al, "The Gene and cDNA for the Human High Affinity Immunoglobulin E Receptor β Chain and Expression of the Complete Human Receptor", The Journal of Biological Chemistry 267(18):12782–12787 (1992).
Newton et al, "Analysis of any point mutation in DNA. The amplification refractory mutation system (ARMS)", Nucleic Acids Research 17(7):2503–2516 (1989).
GenBank/Embl entry (accession No. M89796) Jan. 9, 1995.
Human Molecular Genetics, vol. 5, No. 7, Jul. 1996, pp. 959–962, Hill R. et al, "A new variant of the B subunit of the high–affinity receptor for immunoglobulin in E(FceRi–beta E237G): associations with measures of atropy and bronchial hyper–responsiveness".
Proceedings of the National Academy of Sciences of the USA, vol. 89, No. 8, Apr. 1989, pp. 2766–2770, Orita M. et al, "Detection of polymorphisms of human DNA by gel electrophoresis as single–strand conformation polymorphisms".

*Primary Examiner*—Kenneth R. Horlick
*Assistant Examiner*—Jeffrey Siew
*Attorney, Agent, or Firm*—Nixon & Vanderhye P.C.

[57] ABSTRACT

The invention relates to a method for diagnosing an individual as having atopy or a predisposition thereto. The method involves demonstrating in the individual the presence or absence of either: (i) an unusual variant form of the gene which codes for the beta sub-unit of the high affinity receptor for IgE (FcεRIβ), the variant form comprising a variation in exon (7) which encodes a glycine at amino acid residue 237 instead of glutamic acid which appears at residue 237 in individuals without atopy: or (ii) an unusual polymorphic form of the amino acid sequence for FcεRIβ, the polymorphic form comprising glycine at amino acid residue 237 instead of glutamic acid which appears at residue 237 in individuals without atopy. Materials and other methods relating to the above diagnostic method are also described.

30 Claims, No Drawings

DETECTION OF A VARIANT FORM OF HIGH AFFINITY RECEPTOR TO IGE FCεRIβ USING PRIMERS AND PROBES

The present invention relates to the diagnosis and therapy of atopy and to materials and methods relating thereto.

Atopy is in essence an excessive or misplaced immune response mediated by IgE antibodies in response to common environmental allergens. Common allergens sensitizing atopic individuals are grass and tree pollens, house dust, house dust mites (HDM), bacteria, fungi, feathers, hair, eggs, milk and chocolate. Atopy underlies hayfever, asthma, eczema, urticaria and certain gastro-intestinal disorders.

Asthma is an atopic condition of particular interest as it is becoming more prevalent. It now affects one child in seven in the United Kingdom (Strachan D. P., et al., Arch. Dis. Childhood 70, 174–178, 1994). Allergies/atopy underlies 95% of childhood asthma cases. Asthma may be identified by recurrent wheeze and intermittent airflow limitation. An asthmatic tendency can be quantified by the measurement of bronchial hyper-responsiveness (BHR) in which an individual's dose-response curve to a bronchoconstrictor such as histamine or methacholine is constructed. The curve is commonly summarised by the dose which results in a 20% fall in airflow (PD20) or the slope of the curve between the initial airflow measurement and the last dose given (slope).

In an atopic immune response, IgE is produced by B-cells in response to allergen stimulation. These antibodies coat mast cells by binding to the high affinity receptor for IgE (FcεRI). When a multivalent allergen binds to an IgE coated mast cell, the cross-linking of adjacent IgEs by allergen initiates a series of cellular events leading to the destabilization of the cell membrane and release of inflammatory mediators. This results in mucosal inflammation, wheezing, coughing, sneezing and nasal blockage.

Atopy can be diagnosed by (i) a positive skin prick test in response to a common allergen; (ii) detecting the presence of specific serum IgE for allergen; or (iii) by detecting elevation of total serum IgE. Using these and other assays, a genetic linkage between generalised atopic IgE responses and chromosome 11q has been observed.

Previous studies have found linkage of atopy and bronchial hyper-responsiveness to markers on chromosome 11q13 (eg Cookson, W. O. C. M., et al., 1989 Lancet i pages 1292–1295.) and the beta-chain of the high affinity receptor for IgE (FcεRIβ) has been identified as a candidate gene for this linkage (Sandford, A. J., et al., 1993 Lancet 341, pages 332–334).

WO95/05481 provides further information on atopy and its diagnosis and treatment. In particular, it discloses variants of the gene encoding FcεRIβ which are associated with atopy and it teaches a method for diagnosing atopy which is based upon the demonstration of the presence or absence of one or two variants in a specific portion of the DNA sequence of the gene encoding FcεRIβ. The specific DNA sequence is located near the commencement of exon 6 of the FcεRIβ gene on chromosome 11q and two variants are described. The first variant (designated I181L) encodes a polymorphism in which there is a change of isoleucine to leucine at amino acid residue 181. The second variant (designated I181L/V183L) involves a double mutation that includes the change at residue 181 and the additional change of valine to leucine at residue 183. The amino acid residues 181 and 183 are positioned in the fourth transmembrane domain of FcεRIβ. The variants and polymorphisms are fully described in WO95/05481.

The polymorphisms I181L and I181L/V183L and associated polynucleotide variants have been described in British and Australian populations and are, in selected subjects, associated with atopy and atopic asthma (Shirakawa, T., et al. 1994 Nature Genetics 7, 125–9; and Hill, M. R. et al., 1995 Br. Med. J., 311, 776–779). However the two polymorphisms/variants I181L and I181L/V183L have in practice proved problematical to assay, there being a high false-negative rate for PCR-based tests.

Unexpectedly, the present applicants have found a further variant associated with atopy and atopic asthma which is in the coding sequence for the C-terminal cytoplasmic tail of FcεRIβ (the first quarter of the C-terminal tail is encoded in exon 6 and the remainder in exon 7). This new variant (designated E237G) is located within exon 7 of the FcεRIβ gene. The normal sequence of the FcεRIβ gene has been published in Kuster, H., et al. 1992, J. Biol. Chem., 267, 12782–12787, "The gene and cDNA for the human high affinity immunoglobulin E receptor β chain and expression of the complete human receptor". The sequence can also be found in the Genbank/Embl Databases under Accession No. M89796.

The newly discovered variation in the coding sequence for the C-terminal cytoplasmic tail of FcεRIβ results in a change of glutamic acid to glycine at amino acid residue 237. Sequencing of exon 7 in atopic individuals confirms a nucleotide change from adenine to guanine at nucleotide residue 6843 of the FcεRIβ gene (Kuster et al., 1992 supra.,). For completeness it should be noted that nucleotide residue 6843 of the 1992 Kuster et al sequence, corresponds to nucleotide residue number 7297 in the Genbank/Embl Database sequence.

To data the applicants have investigated 1004 Australian Caucasian individuals in 230 nuclear families for the presence of the E237G polymorphism. 26 males and 26 females were found to have the polymorphism giving a population prevalence of about 5.3%. The E237G polymorphism was significantly associated with increases in (i) skin test responses to house dust mite (p=0.02 by Mann-Whitney U test) and grass pollen (p=0.0008); (ii) radioallergosorbent test specific IgE titres (RAST) to HDM (p=0.001) and grass pollen (p=0.04); and (iii) BHR to metacholine (p=0.0006). The relative risk of children carrying the E237G polymorphism having asthma was 2.4 compared to children without the variant (95% CI 1.29–4.32; p=0.004). Unlike the I181L and I181L/V183L polymorphisms which are maternally linked, the E237G polymorphism is independent of the parental origin of the allele.

In a similar study of individuals in Japan, the E237G polymorphism has also been found to be associated with atopic asthma, there being a particularly high association with childhood asthma (Shirakawa, T. et al., 1996 Human Molecular Genetics, Vol. 5, No. 8 pages 1129 to 1130.).

The high affinity receptor for IgE, FcεRI, is a tetrameric complex formed by an α chain which can bind IgE, a β chain and a homodimer of γ chains. It belongs to a family of receptors that contain homologous activation motifs that appear capable of autonomously triggering cell activation via protein-tyrosine phosphorylation. Two forms of the activation motif appear in FcεRI: one in the β chain and one in the γ chain. They are believed to operate synergistically. Upon triggering of FcεRI, the protein-tyrosine kinase Lyn, already associated with the β chain becomes activated and phosphorylates the β and γ chains. Phosphorylation of the γ chain induces the association of protein-tyrosine kinase Syk with the γ chain and the subsequent activation of Syk that then activates phospholipase (C$^\gamma$ 1 leading to calcium mobilization). The β chain cannot initiate the full signalling capacity of FcεRI. However the importance and unique role of the β chain is demonstrated when the cytoplasmic C-terminal tail is removed with the consequence that signalling is abolished even when the γ dimer is present. This indicates a role for the β chain in controlling receptor phosphorylation. Amino acid residue 237 (the site of the polymorphism) is located adjacent to the immunoreceptor tyrosine activation motif (residues 212–228) reported in the cytoplasmic C-terminal tail of FcεRIβ. The polymorphism E237G introduces a significant hydrophobicity change within the C-terminus of FcεRIβ which may effect the intracellular signalling capacity of FcεRIβ. The substitution of the polar negatively charged glutamic acid at residue 237 with the smaller polar, but uncharged, glycine results in the loss of the hydrophilic nature of this region when examined by the Chou-Fassman hydrophobicity prediction program (GCG Molecular Biology Package, Wisconsin).

Thus the present applicants have unexpectedly established that there is a previously unrecognised variant/polymorphism (in the nucleotide/amino acid sequences respectively) in the cytoplasmic C-terminal tail of FcεRIβ which comprises sequence changes associated with a change of glutamic acid to glycine at amino acid residue 237 and which is associated with atopy and atopic asthma. These new and unexpected teachings make possible new diagnostic methods.

Thus the present invention provides a method for diagnosing an individual as being atopic or asthmatic, or of having a predisposition to atopy or asthma which comprises demonstrating in the individual the presence or absence of an unusual variant form of the gene which codes for FcεRIβ, the variant form encoding a polymorphism comprising glycine at residue 237 instead of glutamic acid.

As an alternative to analysing the gene for a variant, the amino acid sequence may be analysed for the equivalent polymorphism.

Thus the present invention also provides a method for diagnosing an individual as being atopic or asthmatic or of having a predisposition to atopy or asthma which comprises demonstrating in the individual the presence or absence of an unusual polymorphic form of the amino acid sequence for FcεRIβ, the polymorphic form comprising a glycine at residue 237 instead of glutamic acid.

The presence or absence of an unusual polymorphic form of the amino acid sequence for FcεRIβ may be determined by use of a substance which comprises an antibody binding domain which specifically/selectively binds to the unusual polymorphic form which comprises glycine at residue 237 instead of glutamic acid, but not to the normal form of FcεRIβ which occurs in the individuals without symptoms of atopy/asthma. The substance may comprise an antibody, which may be polyclonal or monoclonal.

Where analysis is made at the genetic level, this may be done by employing a technique using one or more nucleic acid sequences which are able to hybridise to the unusual variant form of the gene under suitable stringency conditions. Typically, one or more of such sequences may be used as primers in a detection system comprising a polynucleotide amplification technique such as PCR, ARMS.

The amplification primers may be specific to the unusual variant, but not to wild-type. In which case amplification will only occur if the unusual variant is present in the test sample. Alternatively, the amplification primers may be non-specific. In which case they are used to amplify a sequence region of the variant gene which comprises the nucleotide change(s) which effect the amino acid change at residue 237. Thus an unusual variant such as E237G may be detected by specific PCR using the established techniques of direct sequencing, SSCP and ARMS (Sanger F., et al., 1977 PNAS USA 74: 5463–5467; Orita M., et al., 1989 Genomics 5: 874–879; Newton C. R., et al., 1989 Nucl. Acids Res., 17: 2503–2516).

PCR, ARMS etc may be followed by direct sequencing and sequence analysis, analysis of single stranded conformational polymorphism (SSCP) and/or size analysis of the amplification products where the amplification reaction is designed to amplify a nucleotide sequence the size of which is characteristic of the presence of the unusual variant comprising the nucleotide changes and/or by probing the amplification products with a sequence-specific nucleic acid probe capable of annealing to a portion of the amplified gene which is specific to the unusual variant and not to wild-type. Any suitable method for the confirmation of the existence of a particular nucleotide sequence may be employed and the suggestions given above are for the purposes of illustration only.

DNA or RNA-based amplification methods may be employed. Thus the amplification may be carried out based on mRNA or cDNA made from mRNA.

If primers used are specific to the variant, there will only be successful amplification by eg PCR, ARMS if the variant is present in the test sample. Alternatively the primers used could be non-specific to the variant, the amplification serves only to increase sample material for analysis by a different method such as direct sequencing and SSCP as mentioned above. Suitable nucleic acid sequences for use as specific probes, or specific or non-specific primers in a detection assay for E237G variant/polymorphism as discussed herein can be ascertained from knowledge of the known DNA sequence (Kuster et al., 1992 supra.) and the disclosure of the existence of the variant/polymorphism as provided herein and come within the scope of the present invention.

The teaching of the existence of the E237G variant/polymorphism enables one skilled in the art to easily design and make in accordance with known techniques eg probes and primer pairs based on the publicly available sequence information for FcεRIβ. Similarly a skilled person would be able to ascertain from the publicly available sequence information for FcεRIβ, peptides and polypeptides which may be made and employed in accordance with known techniques, to produce substances comprising an antibody binding domain which specifically/selectively bind to the E237G polymorphic form and fail to bind substantially to the normal form of FcεRIβ which occurs in individuals without symptoms of atopy/asthma.

The patient sampling and assay system (whether assaying polynucleotide or amino acid sequences) may be in accordance with standard techniques in the art. However such assay systems will be newly utilising complementary nucleic acid sequences as probes or primers, or specific antibodies identified by the applicants by virtue of the disclosure of the E237G variant/polymorphism made herein as being useful for the diagnosis of atopy or asthma or a predisposition there towards.

Thus the present invention also provides oligonucleotide hybridisation probes which comprise a sequence of nucleotides with sufficient complementarity and length to enable specific hybridization under suitably high stringency conditions, to a portion of test sample genetic material deriving from an individual patient which comprises the variation in the sequence which gives rise to an unusual E237G form of the gene for the beta sub-unit as discussed above; the probe itself may hybridise to the unusual sequence of nucleotides which can give rise to the variant gene. The oligonucleotide hybridisation probe may not show significant hybridisation to an equivalent portion of test sample genetic material derived from an individual without symptoms of atopy/asthma.

A probe should comprise sufficient nucleotides for efficient and specific annealing in order that the diagnostic analysis be sufficiently accurate. Typically a probe may comprise 17 to 20 nucleotides, but of course the skilled person could prepare probes of other lengths and test them in accordance with known techniques and the disclosures herein for functionality in a given set of suitably high stringency hybridisation conditions. In order to aid detection of specific hybridisation, the probe may be labelled in accordance with techniques well-known in the art.

In the alternative, there are provided nucleic acid sequences with sufficient complementarity and length to enable specific hybridization under suitably high stringency conditions to a portion of test sample genetic material which comprises the variation in the sequence which gives rise to the E237G form of the gene for the beta sub-unit as discussed above, for use as primers in a reaction to amplify the gene. Typically there may be provided a pair of such primers. The amplification reaction may comprise one stage of a diagnostic assay. The hybridization of such primers under suitably high stringency conditions may be to a portion of nucleotide sequence lying in the vicinity of, but upstream and/or downstream of the E237G variant nucleotides which give rise to the unusual form of FcεRIβ. The primers may be non-specific for the E237 variant nucleotides or a primer may be specific for the E237 variant nucleotides. The methods as herebefore described may utilise nucleic acid sequences, probes and primers both as generally described above, or of the specific examples (or functional equivalents thereof) given in the detailed description which follows.

Reference above is made to high-stringency conditions for hybridization. Hybridization is the process whereby two single-stranded polynucleotides anneal to each other to form a double-stranded molecule. The annealment is effected by hydrogen bonding between the complementary bases in the two strands. However under certain reaction conditions (non-stringent conditions) any pair of single-stranded polynucleotides will anneal to each other to form a double-stranded molecule (non-specific hybridization). Under different reaction conditions (high stringency conditions) this non-specific hybridization is reduced or minimised so that hybridization occurs, only between a pair of single-stranded polynucleotides with substantial (if not complete) complementarity to each other. The more stringent the conditions are, the greater complementarity is needed for hybridization. As stringency conditions are decreased, so does the requirement for complementarity.

Thus the skilled person will in accordance with standard techniques identify a set of reaction conditions sufficiently stringent for their particular purpose. Generally of course the aim is to identify by use of one single-stranded polynucleotide sequence as a probe or primer another single-stranded complementary sequence in a test sample which is either exactly complementary or substantially complementary to the probe or primer sequence. The reaction conditions (the high stringency condition) at which the hybridization is adequately specific will also be determined by the length of the single-stranded polynucleotide sequence used as a primer or probe. Where the primer/probe sequence is very short, greater care may be needed in order to avoid non-specific binding and the reaction conditions therefore may need to be highly stringent. The reaction conditions however may need to be less stringent where the primer/probe sequence is long (and therefore likely to be very specific).

It can be seen from the above that 'high-stringency conditions' are variable according to the nature of the primer/probe and whether or not the skilled person is desirous of identifying only exactly complementary sequences or of sequences with incomplete complementary. The skilled person in accordance with standard techniques is able to identify for themselves the high stringency conditions appropriate to their experimental or diagnostic aim.

Analysis may also be made of the amino acid sequence. This may be done by sequencing studies, or by use of a probe comprising an antibody binding domain which is specific for the E237G polymorphism. The probes may comprise antibodies (monoclonal or polyclonal) which may be raised against the unusual E237G polymorphism eg by use of peptides/polypeptides ascertained and made in knowledge of the available sequence information for FcεRIβ as mentioned above. The probes may be labelled in accordance with standard methodologies. In vitro or in vivo diagnosis may be possible. Thus the present invention also provides probes comprising an antibody binding domain which are specific for the E237G polymorphism. Such 'antibody binding domain' probes may not bind to the normal form of FcεRIβ present in individuals without symptoms of atopy/asthma. The probes may be antibodies. They may be polyclonal or monoclonal.

As mentioned above, given knowledge of the amino acid sequence for FcεRIβ and the unusual E237G polymorphic forms associated with atopy or asthma described herein, standard synthesis techniques may be used to manufacture short peptides or longer peptides characteristic of the E237G polymorphism and not of the normal 'wild-type' form in individuals without atopy, for use as immunogens to raise antibodies. In the alternative, the E237G polymorphism associated with atopy or asthma and described herein may be isolated and purified for use as an immunogen to raise antisera. The present invention also therefore provides polypeptides (synthetic or isolated) and immunologically cross-reactive derivatives and fragments eg short peptide sequences which are characteristic of the E237G polymorphism as specifically described therein.

The present invention also provides diagnostic kits and reagents for the detection of atopy or asthma or a predisposition there towards, comprising any of nucleic acid sequences, probes, primers, antibodies, polypeptides or peptides as described above. Also provided is the use of any of nucleic acid sequences, probes, primers, antibodies, polypeptides or peptides as described above in methods as described, or in the manufacture of diagnostic kits and reagents for the detection of atopy or asthma or a predisposition there towards.

In terms of treatment possibilities the disclosure that the E237G polymorphic form of the cytoplasmic C-terminal tail of FcεRIβ is associated with atopy or asthma. enables assays to screen for compounds which down-regulate the unusual polymorphic form. The sequence information provided herein will also enable the development of antisense RNA treatment strategies to block the E237G polymorphism of the cytoplasmic C-terminal tail of FcεRIβ. Antibody based therapies focussing on the E237G polymorphism may also be possible. Use may be made of an antibody, possibly humanised in accordance with known techniques, or of a compound comprising just an antibody domain which is specific for the E237G polymorphism for treatment of an individual with atopy or asthma or a predisposition there towards. In particular, the effect of the unusual polymorphic form of the cytoplasmic C-terminal tail of FcεRIβ on intracellular signalling may identify a novel target for therapeutic intervention.

Thus the present invention also extends to cover use of any of nucleic acid sequences, probes, primers, antibodies, polypeptides or peptides as described above in treatment strategies or in methods to identify compounds of prophylactic or therapeutic value. Invention also extends to any such prophylactic or therapeutic compounds identified by use of the information materials and methods disclosed herein.

In summary, detection of an unusual E237G polymorphic form of the beta sub-unit of FcεRIβ or detection of a coding sequence for said E237G polymorphism is a new and unexpected finding of diagnostic use in predicting/diagnosing atopy and specific atopic conditions such as asthma. If an E237G polymorphism/variant associated with atopy or asthma is detected in an individual preferably at the neonatal stage in accordance with the teachings of the present application, strategies for prevention of atopy or asthma by environmental manipulation to control contact with common allergens and/or vaccination against common allergens can then be devised for the individual concerned.

Furthermore, the E237G polymorphism may also define a subgroup of eg asthma sufferers with a particular clinical course, in which case recognition of the variant/polymorphism would be of value in defining prognosis and management of asthma.

There now follows a more detailed description about testing for the E237G variant in FcεRIβ.

Located in exon 7, E237G lies within the C-terminal cytoplasmic tail of FcεRIβ. The polymorphism is an amino acid change at residue 237 from glutamine acid to glycine. The polymorphism E237G is detected by eg specific PCR using the established techniques of direct sequencing, SSCP and ARMS.

(A) Direct sequencing and Single Stranded Conformational Polymorphism (SSCP)

SSCP is a technique in which DNA is amplified and then split into its two component chains and then moved down a gel by electrophoresis. The presence of a mutation on variant/polymorphism in one of the chains may mean that it forms a different shape (conformation) in the gel and so moves separately from the wild type thereby allowing detection.

A sample of patient blood is taken and peripheral blood leucocytes obtained in accordance with standard techniques. DNA is extracted from the leucocytes by standard techniques (see eg Blin, N., et al., 1976 Nucleic Acids Research., Vol. 3, page 2303: "A general method for isolation of high molecular weight DNA from eukaryotes").

Direct sequencing and SSCP involves a two round PCR (two rounds is not essential, but it provides a cleaner product) with a common first round. For direct sequencing the second round incorporates a biotinylated primer.

Schematically:

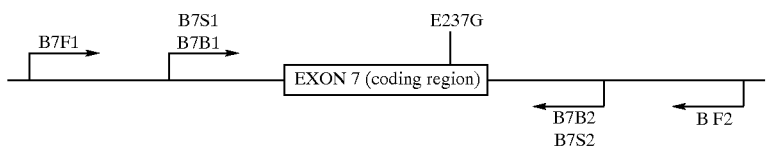

```
Primer pairs                                                                   Product size
1st round             5'                                                  3'
           B7F1:      CCA GCT AGT CTG GTT TGG TTT    (SEQ ID NO:1)         515 bp
           B7F2:      ATT AAG GTG GAC AGA AGC AGC    (SEQ ID NO:2)

2nd round
5'-3' sequencing  B7S1:   GAT GAG GTA AGT CTC TTG AG  (SEQ ID NO:3)        238 bp
                 *B7B2:   AAC CTT GGC CTT CTG GAT     (SEQ ID NO:4)
3'-5' sequencing *B7B1:   TGA GGT AAG TCT CTT GAG     (SEQ ID NO:5)        238 bp
                  B7S2:   CAA AAC CTT GGC CTT CTG G   (SEQ ID NO:6)
```

-continued

| Primer pairs | | | Product size |
|---|---|---|---|
| SSCP | B7S1: | GAT GAG GTA AGT CTC TTG AG (SEQ ID NO:7) | 240 bp |
| | B7S2: | CAA AAC CTT GGC CTT CTG G (SEQ ID NO:8) | |

(*5' biotinylated primer)

PCR reaction mixture

1st round 10 μl per reaction volume: Template is 50–100 ng genomic DNA.

2nd round 50 μl per reaction volume: Template is 1 μl 1st round product diluted ×100 in dH$_2$O.

Reaction mixture for 1st and 2nd round: 0.1 μg each primer, 200 μM dNTP, 50 mM KCl, 10 mM Tris-HCl (pH 8.3), 1.5 mM MgCl$_2$ and 0.2 units Taq polymerase (Boehringer Mannheim).

PCR conditions

| 1st round | 2nd round |
|---|---|
| 94° C. 5.0 minute 1 cycle | 94° C. 5.0 minute 1 cycle |
| 94° C. 1.0 minute | 94° C. 1.0 minute |
| 59° C. 1.0 minute 35 cycle | 50° C. 0.5 minute 20 cycle |
| 72° C. 1.0 minute | 72° C. 0.5 minute |
| 72° C. 10.0 minute 1 cycle | 72° C. 10.0 minute 1 cycle |

(Ai) Direct sequencing

Preparation of single strand template DNA

Single strand template is prepared from 40 μl 2nd round PCR product using streptavidin coated magnetic beads (Dynabeads, Dynal UK Ltd) following manufacturer's instructions.

Sequencing

Performed using Sequenase Version 2.0 DNA Sequencing Kit (Amersham LIFE SCIENCE) and [α-$^{35}$S] dATP radionucleotide following suggested protocol. Sequencing primer used is the non-biotinylated primer of the 2nd round PCR. Sequencing in either direction detects E237G and it is sometimes useful to perform both as confirmation when heterozygote sequence appears faint.

(Aii) SSCP

Using Bio-Rad Protean II Cell apparatus (Bio-Rad Laboratories Ltd, UK), 4 μl of second round PCR product was electrophoresed at 10 W per gel at 4° C. for 22 hours in a 10% (w/v) polyacrylamide (19: 1 acrylamide: bis)/10% (v/v) glycerol gel with 1× TBE buffer. DNA was visualized by silver staining using a Bio-Rad Silver Stain Kit (Bio-Rad Laboratories Ltd, UK) and then gels were vacuum-dried onto Whatman 3M paper (Merck Ltd).

(B) ARMS

Primers

B7FA1 (SEQ ID NO: 9): TGG CCA GCT AGT CTG GTT TGG TTT TCT GGA

B7FA2 (SEQ ID NO: 10): GGA GCA TAT TAA GGT GGA CAG AAG CAG CAG

B7M1 (SEQ ID NO: 11): ATT CAG CTA CTT ACA GTG AGT TGG AAG ACC CAG GCG G

B7W2 (SEQ ID NO: 12): CAC GTG ATT CTT ATA AAT CAA TGG GAG GAG ACA ATT

Schematically:

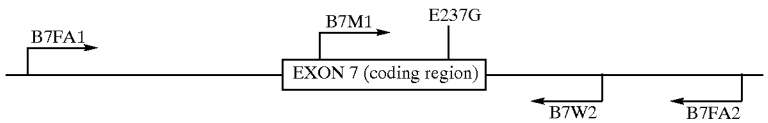

PCR reaction mixture

50 μl reaction volume: 0.1–0.2 μg genomic DNA, 250 ng of primers B7FA1, B7FA2, B7W2 and 125 ng of primer B7M1, 200 μM dNTP, 50 mM Kcl, 10 mM Tris-HCl (pH 8.3), 1,5 mM MgCl$_2$ and 0.2 units Taq polymerase (Boehringer Mannheim).

PCR conditions

A Hot start is recommended, Taq polymerase being added in 20% of the final volume of PCR reaction mixture after the first cycle which is held at 80° C.

94° C. 5.0 minute 1 cycle (Hold at 80° C., add Taq)

94° C. 1.0 minute

60° C. 2.0 minute 35 cycle

72° C. 2.0 minute

72° C. 10.0 minute 1 cycle

Genotyping

Amplified product is visualized in an ethidium stained 4% agarose gel (3.0 g NuSieve* GTG (Flowgen), 1.0 g LMP agarose (GIBCO BRL), 50 μg ethidium bromide per 100 ml 0.5× TBE) run for two hours at 60 V. In addition to the 446 bp control band, if present wild type sequence will result in a 280 bp band and E237G sequence in a 238 bp band.

For any additional general guidance on interpreting the detailed instruction given above, reference may be made to Sanger F. et al., 1977 supra., Orita M., et al., 1989 supra and Newton C. R., et al., 1989 supra., or to standard texts such as Short Protocols in Molecular Biology Second Edition A Compendium of Methods from Current Protocols in Molecular Biology edited by Frederick M. Ausubel et al. and Molecular Cloning, A Laboratory Manual eds Sambrook, Fritsch and Maniatis, Cold Spring Harbor Laboratory Press, 1989.

What is claimed is:

1. A method for diagnosing an individual as having atopy or a predisposition thereto, which comprises demonstrating in the individual the presence or absence of either: (i) a variant form of the gene which codes for the beta sub-unit of the high affinity receptor for IgE (FcεRIβ), the variant form comprising a variation in exon 7 which encodes a glycine at amino acid residue 237 instead of glutamic acid which appears at residue 237 in individuals without atopy; or (ii) a polymorphic form of the amino acid sequence for FcεRIβ, the polymorphic form comprising glycine at amino acid residue 237 instead of glutamic acid which appears at residue 237 in individuals without atopy.

2. A method according to claim 1 which comprises the steps of:
   obtaining a suitable tissue sample from the individual;
   preparing from the tissue sample a nucleic acid sample; and
   probing or analysing the nucleic acid sample for the presence or absence of said variant form of the gene which encodes FcεRIβ.

3. A method according to claim 2 wherein prior to said probing or analysis, said gene which encodes the variant form of the FcεRIβ gene is amplified.

4. A method according to claim 3 wherein amplification is by PCR.

5. A method according to claim 4 wherein the PCR amplification is carried out using a pair of oligonucleotide primers and a first member of the primer pair comprises a nucleotide sequence which hybridises under suitably stringent conditions to a substantially complementary nucleotide sequence which is proximal to, and 5' of, the codon for amino acid residue number 237 and the second member of the primer pair comprises a nucleotide sequence which hybridises under suitably stringent conditions to a substantially complementary nucleotide sequence which is proximal to, and 3' of, the codon for amino acid residue number 237.

6. A method according to claim 3 wherein the amplification is carried out using a pair of oligonucleotide primers and a member of the primer pair comprises a nucleotide sequence which itself hybridises under suitably stringent conditions to the sequence of nucleotides which give rise to said variant gene, such that amplification will only proceed when said variant gene is present in the sample.

7. A method according to claim 2 which comprises probing the nucleic acid sample with an oligonucleotide hybridisation probe which under suitable conditions of high stringency only shows substantial hybridisation to said variant gene and not to the equivalent gene in individuals without atopy, such that hybridisation only occurs when the said variant gene is present in the sample.

8. A method according to claim 2 wherein the analysis of the nucleic acid sample for the presence or absence of said variant gene is carried out by direct sequencing of the gene sequence which encodes the E237G polymorphism, and wherein the nucleotide sequences for 5' to 3' and 3' to 5' sequencing are amplified prior to said direct sequencing.

9. A method according to claim 2 wherein the analysis of the nucleic acid sample for the presence or absence of said variant gene is carried out by single stranded conformational polymorphism (SSCP) analysis.

10. A method according to claim 1 wherein the presence or absence of the polymorphic form of the amino acid sequence for FcεRIβ is established by use of a substance which comprises an antibody binding domain which is specific for the polymorphic form.

11. A method according to claim 10 wherein the substrate comprises an antibody.

12. A method according to claim 11 wherein the antibody is either monoclonal or polyclonal.

13. An oligonucleotide hybridization probe for diagnosing an individual as having atopy or a predisposition thereto, which probe comprises a sequence of nucleotides such that under suitably stringent conditions the probe: (i) specifically binds to a variant form of the gene which codes for FcεRIβ the variant form comprising a variation in exon 7 which binds to said probe and encodes a glycine at amino acid residue 237 instead of glutamic acid which appears at residue 237 in individuals without atopy; and (ii) fails to show significant hybridization to genetic material derived from individuals lacking said variant form of said gene.

14. A pair of oligonucleotide primers for amplification of a variant form of the gene which codes for FcεRIβ, for diagnosing an individual as having atopy or a predisposition thereto, wherein the variant form comprises a variation in exon 7 which encodes a glycine at amino acid 237 instead of glutamic acid which appears at residue 237 in individuals without atopy; wherein a single member of the primer pair comprises a nucleotide sequence which itself hybridises under suitable stringent conditions to the sequence of nucleotides which give rise to said variant gene such that an amplification reaction employing such a member of a primer pair will only proceed where said variant gene is present in a sample.

15. A pair of primers according to claim 14 which is an amplification system function to amplify said variant form, but fail to significantly amplify genetic material derived from individuals without atopy.

16. An assay kit which comprises an oligonucleotide hybridisation probe according to claim 13.

17. An assay kit which comprises a pair of oligonucleotide primers according to any one of claims 14 or 15.

18. An assay kit which comprises an oligonucleotide hybridisation probe comprising a sequence of nucleotides such that under suitably stringent conditions the probe: (i) specifically binds to a variant form of the gene which codes for FcεRIβ the variant form comprising a variation in exon 7 which binds to said probe and encodes a glycine at amino acid residue 237 instead of glutamic acid which appears at residue 237 in individuals without atopy; and (ii) fails to show significant hybridization to genetic material derived from individuals lacking said variant form of said gene along with a pair of oligonucleotide primers according to any one of claims 14 or 15.

19. A method for diagnosing an individual as having atopy or a predisposition thereto, which comprises demonstrating in the individual the presence or absence of either: (i) a variant form of the gene which codes for the beta sub-unit of the high affinity receptor for IgE (FcεRIβ), the variant form comprising a variation in exon 7 at a nucleotide corresponding to nucleotide 7297 of the nucleic acid sequence deposited under GenBank/Embl accession number M89796, which variation causes the codon in which it appears to encode glycine instead of glutamic acid which is encoded by the equivalent codon in individuals without atopy; or (ii) a polymorphic form of the amino acid sequence for FcεRIβ, the polymorphic form comprising glycine at the amino acid residue which corresponds to the codon of the nucleic acid sequence deposited under GenBank/Embl accession number M89796 which includes nucleotide 7297, instead of glutamic acid which appears at that residue in individuals without atopy.

20. A method according to claim 19 which comprises the steps of:
   obtaining a suitable tissue sample from the individual;
   preparing from the tissue sample a nucleic acid sample; and
   probing or analyzing the nucleic acid sample for the presence or absence of said variant form of the gene which encodes FcεRIβ.

21. A method according to claim 20 wherein prior to said probing or analysis, said gene which encodes the variant form of the FcεRIβ gene is amplified.

22. A method according to claim 21 wherein amplification is by PCR.

23. A method according to claim 22 wherein the PCR amplification is carried out using a pair of oligonucleotide primers and a first member of the primer pair comprises a nucleotide sequence which hybridizes under suitably stringent conditions to a substantially complementary nucleotide sequence which is proximal to, and 5' of, the codon for amino acid residue number 237 and the second member of the primer pair comprises a nucleotide sequence which hybridizes under suitably stringent conditions to a substantially complementary nucleotide sequence which is proximal to, and 3' of, the codon for amino acid residue number 237.

24. A method according to claim 21 wherein the amplification is carried out using a pair of oligonucleotide primers and a member of the primer pair comprises a nucleotide sequence which itself hybridizes under suitable stringent conditions to the sequence of nucleotides which give rise to said variant gene, such that amplification will only proceed when said variant gene is present in the sample.

25. A method according to claim 20 which comprises probing the nucleic acid sample with an oligonucleotide hybridization probe which under suitable conditions of high stringency only shows substantial hybridization to said variant gene and not to the equivalent gene in individuals without atopy, such that hybridization only occurs when the said variant gene is present in the sample.

26. A method according to claim 20 wherein the analysis of the nucleic acid sample for the presence or absence of said variant gene is carried out by directing sequencing of the gene sequence which encodes the E237G polymorphism, and wherein the nucleotide sequences for sequencing are amplified prior to said direct sequencing.

27. A method according to claim 20 wherein the analysis of the nucleic acid sample for the presence or absence of said variant gene is carried out by single stranded conformational polymorphism (SSCP) analysis.

28. A method according to claim 19 wherein the presence or absence of the polymorphic form of the amino acid sequence for FcεRIβ is established by use of a substance which comprises an antibody binding domain which is specific for the polymorphic form.

29. A method according to claim 28 wherein the substance comprises an antibody.

30. A method according to claim 29 wherein the antibody is either monoclonal or polyclonal.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
ccagctagtc tggtttggtt t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
attaaggtgg acagaagcag c                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gatgaggtaa gtctcttgag                                                20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 4
aaccttggcc ttctggat                                                  18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
tgaggtaagt ctcttgag                                                  18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
caaaaccttg gccttctgg                                                 19

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: Primer

<400> SEQUENCE: 7
gatgaggtaa gtctcttgag                                              20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
caaaaccttg gccttctgg                                               19

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
tggccagcta gtctggtttg gttttctgga                                   30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
ggagcatatt aaggtggaca gaagcagcag                                   30

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 11
attcagctac ttacagtgag ttggaagacc caggcgg                           37

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 12
cacgtgattc ttataaatca atgggaggag acaatt                            36
```